(12) United States Patent
Prezado et al.

(10) Patent No.: US 11,235,174 B2
(45) Date of Patent: Feb. 1, 2022

(54) MINIBEAM RADIOTHERAPY DEVICE

(71) Applicants: CENTRE NATIONAL DE LA RECHERCHE SCIENTIFIQUE, Paris (FR); UNIVERSITE PARIS-SUD, Orsay (FR); UNIVERSITE PARIS DIDEROT, Paris (FR)

(72) Inventors: Yolanda Prezado, Paris (FR); Morgane Dos Santos, Chatenay Malabry (FR); Batiste Janvier, Evry (FR)

(73) Assignees: CENTRE NATIONAL DE LA RECHERCHE SCIENTIFIQUE, Paris (FR); UNIVERSITE PARIS-SUD, Orsay (FR); UNIVERSITE PARIS DIDEROT, Paris (FR)

( * ) Notice: Subject to any disclaimer, the term of this patent is extended or adjusted under 35 U.S.C. 154(b) by 193 days.

(21) Appl. No.: 16/349,938

(22) PCT Filed: Nov. 2, 2017

(86) PCT No.: PCT/EP2017/078096
§ 371 (c)(1),
(2) Date: May 14, 2019

(87) PCT Pub. No.: WO2018/091280
PCT Pub. Date: May 24, 2018

(65) Prior Publication Data
US 2019/0275350 A1    Sep. 12, 2019

(30) Foreign Application Priority Data
Nov. 17, 2016 (FR) ...................... 1661147

(51) Int. Cl.
*A61N 5/10*    (2006.01)
*G21K 1/02*    (2006.01)

(52) U.S. Cl.
CPC ........... *A61N 5/1045* (2013.01); *G21K 1/025* (2013.01)

(58) Field of Classification Search
CPC .............................. G21K 1/025; A61N 5/1045
See application file for complete search history.

(56) References Cited

U.S. PATENT DOCUMENTS

| | | | | |
|---|---|---|---|---|
| 4,166,220 A | * | 8/1979 | Stutts | G21K 1/04 378/147 |
| 4,672,648 A | * | 6/1987 | Mattson | G21K 1/025 378/149 |

(Continued)

FOREIGN PATENT DOCUMENTS

| | | |
|---|---|---|
| JP | S4944839 B1 | 11/1974 |
| JP | 2013195407 A | 9/2013 |
| WO | 2016201557 A1 | 12/2016 |

OTHER PUBLICATIONS

French Search Report from French Patent Application No. 1661147, dated Sep. 29, 2017.

(Continued)

*Primary Examiner* — Chih-Cheng Kao
(74) *Attorney, Agent, or Firm* — Greer, Burns & Crain, Ltd.

(57) ABSTRACT

Device including a multileaf collimator, the multileaf collimator including an array of leaves and slits, the array having an alternation of leaves and slits and extending in a longitudinal direction, the longitudinal direction being defined as a direction extending from an entrance plane of the array toward an exit plane of the array, each leaf being located between two slits; the device having a source for emitting an incident electromagnetic beam or a source for emitting an incident beam of subatomic particles, the source being arranged to emit the beam in the direction of the entrance plane of the array, the multileaf collimator being arranged to (Continued)

obtain an arrangement of beams from the incident beam, and the arrangement of beams forms an alternation of high-energy lines and lower-energy lines.

29 Claims, 3 Drawing Sheets

(56) References Cited

U.S. PATENT DOCUMENTS

| | | | | |
|---|---|---|---|---|
| 5,099,134 | A * | 3/1992 | Hase | G21K 1/025 |
| | | | | 250/363.1 |
| 6,272,201 | B1 * | 8/2001 | Pan | A61B 6/032 |
| | | | | 378/19 |
| 6,421,420 | B1 * | 7/2002 | Grodzins | G21K 1/025 |
| | | | | 378/98.6 |
| 2008/0049897 | A1 | 2/2008 | Molloy | |
| 2014/0037062 | A1 * | 2/2014 | Elgort | A61N 5/1049 |
| | | | | 378/63 |
| 2016/0045767 | A1 * | 2/2016 | Bender | G21K 1/025 |
| | | | | 378/149 |
| 2020/0038685 | A1 * | 2/2020 | Kundapur | G21K 1/025 |

OTHER PUBLICATIONS

International Search Report from International Patent Application No. PCT/EP2017/078096, dated Feb. 8, 2018.

* cited by examiner

MINIBEAM RADIOTHERAPY DEVICE

BACKGROUND

The present invention relates to the field of minibeam radiotherapy, a type of radiotherapy based on the spatial fractionation of energy. The present invention relates in particular to a device, comprising a collimator, allowing minibeams to be generated starting from an incident beam. The minibeams form an alternation of high-energy zones and lower-energy zones.

The main application of minibeam radiotherapy is in the field of the treatment of local cancerous tumours and in particular in cases where tumours are located in regions where surgical interventions are inadvisable. Minibeam radiotherapy makes the treatment of the tumour more effective by allowing a higher total dose to be delivered than with the beams in conventional radiotherapy, while offering enhanced preservation of the surrounding healthy tissues.

The microbeam radiotherapy technique has long been known in the state of the prior art. This technique is particularly suitable for treating local cancerous tumours. For delivering higher doses to the tumour while sparing the surrounding healthy tissues as far as possible, the microbeam radiotherapy method is known, which consists of using beams under 1 mm and comprising an alternation of lines.

However, the devices for applying microbeams as described in the state of the prior art are essentially based on the use of an incident beam originating from synchrotron radiation.

This type of radiation is generated by accelerators, which have several drawbacks and are more generally unsuitable for the treatment of patients. Firstly, beam access time is expensive and limited. The costs of synchrotron accelerators are prohibitive. Moreover, there are few synchrotron installations, they are of great complexity and require many highly qualified technicians for maintaining them. Finally, taking into account that these installations cannot be moved, they are therefore remote from the other medical equipment required during treatment by radiotherapy.

An aim of the invention is to propose a less expensive device that can be produced on an industrial scale.

Another aim of the invention is to propose a device of reduced size that can be installed in a hospital facility.

Another aim of the invention is to propose a device that is simpler to operate and maintain.

SUMMARY

These aims are achieved with a multileaf collimator comprising an array of leaves and slits, said array comprising an alternation of leaves and slits and extending in a longitudinal direction, said longitudinal direction being defined as a direction extending from an entrance plane of the array to an exit plane of the array, each leaf being located between two slits; said multileaf collimator being characterized in that:
  at least one leaf of the array has a thickness that is different from a thickness of at least one other leaf of the array in the entrance plane of the array, and/or
  at least one leaf of the array has a thickness that is different from a thickness of at least one other leaf of the array in the exit plane of the array, and/or
  at least one slit of the array has a thickness that is different from a thickness of at least one other slit of the array in the entrance plane of the array, and/or
  at least one slit of the array has a thickness that is different from a thickness of at least one other slit of the array in the exit plane of the array, and/or
  a thickness of at least one leaf of the array varies in the longitudinal direction, and/or
  a thickness of at east one slit of the array varies in the longitudinal direction.

The multileaf collimator according to the invention may have a channel extending in the longitudinal direction and located upstream of the entrance plane of the array.

The thickness of each of the leaves of the array in any one of the planes perpendicular to the longitudinal direction may be greater than 300 µm and/or less than 2 mm.

A distance, in the longitudinal direction, between the entrance plane of the array and the exit plane of the array may be greater than 1 cm and/or less than 6 cm.

At least one leaf of the array may have a thickness that is different from a thickness of at least one other leaf of the array in the entrance plane of the array.

At least one leaf of the array may have a thickness that is different from a thickness of at least one other leaf of the array in the exit plane of the array.

At least one leaf of the array may have a thickness in the entrance plane of the array that is different from a thickness in the exit plane of the array.

The multileaf collimator according to the invention may comprise at least 3 slits and/or at least 2 leaves.

The thickness of each of the slits of the array in any one of the planes perpendicular to the longitudinal direction may be greater than 300 µm and/or less than 1 mm.

At least one slit of the array may have a thickness in the entrance plane of the array that is different from a thickness of at least one other slit of the array in the entrance plane of the array.

At least one slit of the array may have a thickness in the exit plane of the array that is different from a thickness of at least one other slit of the array in the exit plane of the array.

At least one slit of the array may have a thickness in the entrance plane of the array that is different from a thickness in the exit plane of the array.

The successive leaves and/or slits of the array may have respective thicknesses in any one of the planes perpendicular to the longitudinal direction that vary in an increasing manner or that constant with increasing distance from a central plane of the array in two opposite directions perpendicular to the central plane of the array, the central plane of the array being parallel to the longitudinal direction and linking two opposite internal walls of the multileaf collimator between which the leaves extend.

The successive slit/leaf interfaces may form respective angles with respect to a central plane of the array that vary in an increasing manner or that remain constant with increasing distance from the central plane of the array in two opposite directions perpendicular to the central plane of the array, each of these angles having its vertex upstream of the entrance plane of the array with respect to the longitudinal direction, the central plane of the array being parallel to the longitudinal direction and linking two opposite internal walls of the multileaf collimator between which the leaves extend.

The array may be symmetrical with respect to the central plane of the array.

The multileaf collimator according to the invention may comprise a stopper designed to be fitted detachably on the collimator downstream of the exit plane of the array with respect to the longitudinal direction, said stopper being arranged for delimiting a size and/or shape of an arrangement of beams leaving the multileaf collimator.

According to another aspect of the invention, a device is proposed comprising a multileaf collimator according to the invention, said device being characterized in that it comprises a source of emission of an incident electromagnetic beam and/or a source of emission of an incident beam of subatomic particles, said source being arranged for emitting the beam in the direction of the entrance plane of the array, said multileaf collimator being arranged for obtaining an arrangement of beams starting from the incident beam.

The source may emit a divergent incident beam.

The arrangement of beams may have a width greater than 1 mm and/or less than 10 cm.

The arrangement of beams may form an alternation of high-energy lines and lower-energy lines.

The source of electromagnetic radiation may be an X-ray source.

The X-ray source may be a cathode source.

According to another aspect of the invention, a method is proposed for making a multileaf collimator according to the invention, said multileaf collimator being intended to be incorporated in a device according to the invention, said method being characterized in that it comprises:
  acquisition, in technical calculation means, of parameters characterizing a source,
  acquisition, in the technical calculation means, of parameters characterizing respectively:
    a desired arrangement of beams leaving the multileaf collimator and/or at the level of a target, or
    the multileaf collimator,
  optionally acquisition, in the technical calculation means, of parameters characterizing the target,
  at least one step of calculation, by the technical calculation means, of characteristics respectively:
    of the multileaf collimator as a function of parameters acquired in particular concerning the desired arrangement of beams, or
    of the desired arrangement of beams, by successive iterations of the step of acquisition of the parameters characterizing the collimator.

The at least one calculation step may be carried out on the basis of a Monte-Carlo algorithm.

The acquired parameters characterizing a desired arrangement of beams or the calculated characteristics of the desired arrangement of beams may comprise:
  a size of the arrangement of beams, and/or
  a full width at half maximum of a high-energy line, and/or
  a full width at half maximum of a low-energy line, and/or
  a ratio of the maximum energy of a high-energy line to the maximum energy of a low-energy line.

The parameters characterizing the source may comprise:
  a voltage of the source, and/or
  a current of the source, and/or
  a mean dose rate of the source, and/or
  a divergence of the source, and/or
  a field size of the source.

The parameters acquired characterizing the multileaf collimator or the calculated characteristics of the multileaf collimator may comprise:
  a number of slits, and/or
  a number of leaves, and/or
  a length of the channel, in the longitudinal direction, between an inlet of the channel and the entrance plane of the array, and/or
  a distance, in the longitudinal direction, between the entrance plane of the array and the exit plane of the array, and/or
  a thickness of each leaf as a function of a coordinate in the longitudinal direction, and/or
  a thickness of each slit as a function of a coordinate in the longitudinal direction.

The at least one calculation step may further comprise calculation of the relative positions of the source, of the multileaf collimator and/or of the target.

BRIEF DESCRIPTION OF THE DRAWINGS

Other advantages and characteristics of the invention will become apparent on reading the detailed description of implementations and embodiments which are in no way limitative, and from the attached drawings, in which.

DETAILED DESCRIPTION

Figure 1:
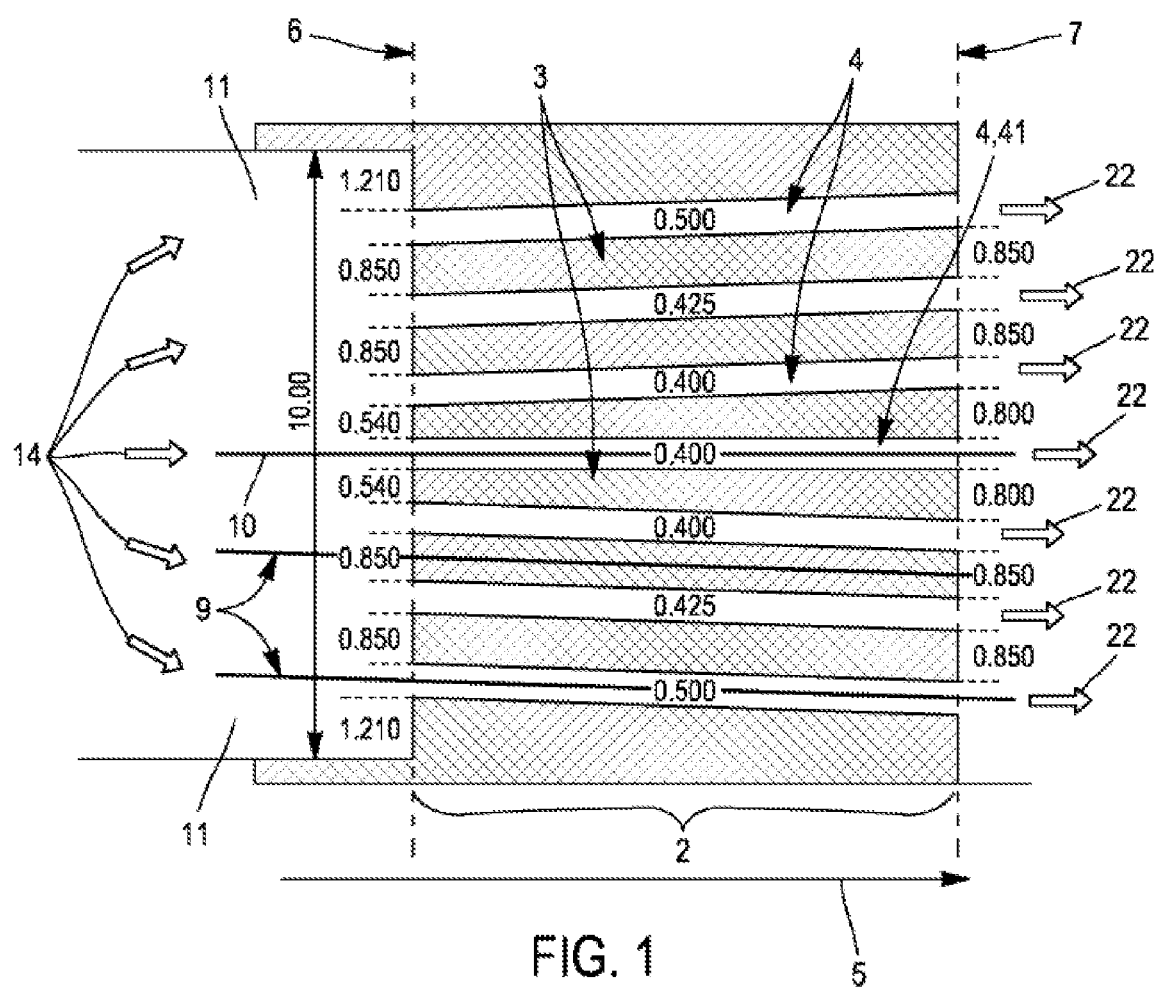
FIG. 1 is a diagrammatic representation of a sectional profile view of the array of leaves and slits of a multileaf collimator according to the invention.

As this embodiment is in no way limitative, variants of the invention can be considered in particular, comprising only a selection of the characteristics described hereinafter, in isolation from the other characteristics described (even if this selection is isolated within a phrase containing other characteristics), if this selection of characteristics is sufficient to confer a technical advantage or to differentiate the invention with respect to the state of the prior art. This selection comprises at least one, preferably functional, characteristic without structural details, or with only a part of the structural details if this part alone is sufficient to confer a technical advantage or to differentiate the invention with respect to the state of the prior art.

An embodiment of multileaf collimator 1 according to the invention comprising an array 2 of leaves 3 and slits 4, and a device 12 comprising the multileaf collimator 1, will now be described, with reference to FIGS. 1 to 5.

The array 2 comprises an alternation of leaves 3 and slits 4 and extends in a longitudinal direction 5.

Each of the leaves 3 and slits 4 extends at least partly (more exactly mainly) in the longitudinal direction 5, but may in addition extend with a component perpendicular to the longitudinal direction 5.

The longitudinal direction is defined as a direction extending from an entrance plane 6 of the array 2 to an exit plane 7 of the array 2, each leaf 3 being located between two slits 4.

By longitudinal direction 5 is meant in the present description a single direction:
- not needing to be parallel to the mid-plane 9 of at least one leaf 3 and/or of at least one slit 4 but
- being parallel to the mid-plane 10 of one of the slits 4 (called central slit 41) or of one of the leaves 3 (called central leaf) corresponding to the central plane 10 of the array 2.

The central plane 10 of the array 2 is parallel to the longitudinal direction 5 and links two opposite internal walls 8 of the multileaf collimator 1 between which the leaves 3 extend.

The mid-plane 9, of a leaf 3 or of a slit 4, comprises:
- a median, of said leaf 3 or of said slit 4, extending in a direction linking the two opposite internal walls 8 between which the leaves 3 extend in the entrance plane 6 of the array 2, and
- a median, of said leaf 3 or of said slit 4, extending in a direction linking the two opposite internal walls 8 between which the leaves 3 extend in the exit plane 7 of the array 2.

According to the embodiment presented, the entrance plane 6 of the array 2 and the exit plane 7 of the array 2 are parallel to one another.

The longitudinal direction 5 is perpendicular to the entrance plane 6 of the array 2.

The longitudinal direction 5 is perpendicular to the exit plane 7 of the array 2.

According to the embodiment, the multileaf collimator 1 is made of brass by spark erosion machining.

In the present description, the thickness of a leaf 3 or of a slit 4 is defined as being measured:
- in a plane (preferably in the entrance plane 6, the exit plane 7, or in any intermediate plane parallel to plane 6 and/or 7), and
- along an axis perpendicular to the direction linking the two opposite internal walls 8 of the multileaf collimator 1 between which this leaf 3 or this slit 4 extends.

The dimensions, in particular the thicknesses of slits 4 and of leaves 3 indicated in FIG. 1, are in millimetres.

In the embodiment presented, at least one leaf 3 (more exactly several leaves 3, more exactly each leaf 3) of the array 2 of the multileaf collimator 1 has a thickness that is different from a thickness of at least one other leaf 3 of the array 2 in the entrance plane 6 of the array 2.

According to the embodiment illustrated in FIG. 1, at least one leaf 3 (more exactly several leaves 3, more exactly each leaf 3) of the array 2 of the multileaf collimator 1 has a thickness that is different from a thickness of at least one other leaf 3 of the array 2 in the exit plane 7 of the array 2.

At least one slit 4 (more exactly several slits 4, more exactly each slit 4) of the array 2 has a thickness that is different from a thickness of at least one other slit 4 of the array 2 in the entrance plane 6 of the array 2.

It should also be noted that at least one slit 4 (more exactly several slits 4, more exactly each slit 4) of the array 2 has a thickness that is different from a thickness of at least one other slit 6 of the array 2 in the exit plane 7 of the array 2.

Each slit 4 has a thickness that remains constant in the longitudinal direction.

Finally, it is noted that a thickness of at least one leaf 3 (more exactly of several leaves 3, at least those nearest to plane 10) of the array 2 varies in the longitudinal direction 5.

At least one leaf 3 (more exactly several leaves 3, at least those nearest to plane 10) of the array 2 has a thickness in the entrance plane 6 of the array 2 different from a thickness in the exit plane 7 of the array 2.

Advantageously, the thickness of each of the leaves 3 of the array 2 in any one of the planes perpendicular to the longitudinal direction 5 is comprised between 300 µm and 2 mm. The thickness of each of the leaves 3 of the array 2 in any one of the planes perpendicular to the longitudinal direction 5 is preferably comprised between 500 µm and 1.3 mm, this thickness being comprised between 540 and 850 µm in the embodiment illustrated in FIG. 1.

In the present description, any range of values includes the limit or boundary values of this range.

Advantageously, the thickness of each of the slits 4 of the array 2 in any one of the planes perpendicular to the longitudinal direction 5 is between 300 µm and 1 mm. The thickness of each of the slits 4 of the array 2 in any one of the planes perpendicular to the longitudinal direction 5 is preferably comprised between 350 and 550 µm, this thickness being between 400 and 500 µm in the embodiment shown in FIG. 1.

In the embodiment as illustrated in FIG. 1:
- the successive adjacent leaves 3 of the array 2 have respective thicknesses in any one of the planes perpendicular to the longitudinal direction 5 that vary in an increasing manner or that remain constant with increasing distance from a central plane (or plane of symmetry) 10 of the array 2 in two opposite directions perpendicular to the central plane 10 of the array 2, and/or
- the successive adjacent slits 4 of the array 2 have respective thicknesses in any one of the planes perpendicular to the longitudinal direction 5 that vary in an increasing manner or that remain constant with increasing distance from a central plane (or plane of symmetry) 10 of the array 2 in two opposite directions perpendicular to the central plane 10 of the array 2, the central plane 10 of the array 2 being parallel to the longitudinal direction 5 and linking the two opposite internal walls 8 of the multileaf collimator 1 between which the leaves 3 extend.

In the particular embodiment presented in FIG. 1, the central plane 10 of the array 2 is parallel to the longitudinal direction 5 and comprises:
- a median, of an entrance face 6 of the array 2, extending between two opposite faces 8 between which the leaves 3 of the array 2 extend,
- a median, of an exit face of the array 2, extending between two opposite faces 8 between which the leaves 3 of the array 2 extend.

The entrance face and the exit face are defined by the perimeter 21 of the array 2, respectively in the entrance plane 6 of the array 2 and in the exit plane 7 of the array 2.

The central plane 10 of the array 2 is merged with the mid-plane 9 of the central slit 4, 41 comprising the central plane 10 of the array 2.

As illustrated in FIG. 1, the central plane 10 of the array 2 constitutes a plane of symmetry:
- of the entrance face of the array 2, and/or
- of the exit face of the array 2, and/or
- of any face parallel to the entrance face and/or to the exit face of the array 2 and between the entrance face and the exit face of the array 2.

It should be noted that according to the embodiment presented in FIG. 1, the successive adjacent slit/leaf interfaces (i.e. between a leaf 3 and a slit 4 or vice versa) form respective angles with respect to a central plane 10 of the array 2 that vary in an increasing manner or that remain constant with increasing distance from the central plane 10 of the array 2 in two opposite directions perpendicular to the central plane 10 of the array 2, each of these angles having its vertex upstream of the entrance plane 6 of the array 2 with respect to the longitudinal direction 5 (i.e. on the side opposite the array 2 with respect to plane 6), the central plane 10 of the array 2 being parallel to the longitudinal direction 5 and linking the two opposite internal walls 8 of the multileaf collimator 1 between which the leaves 3 of the array 2 extend.

According to the embodiment as illustrated in FIG. 1, the array 2 is symmetrical with respect to the central plane 10 of the array 2.

Figure 2:
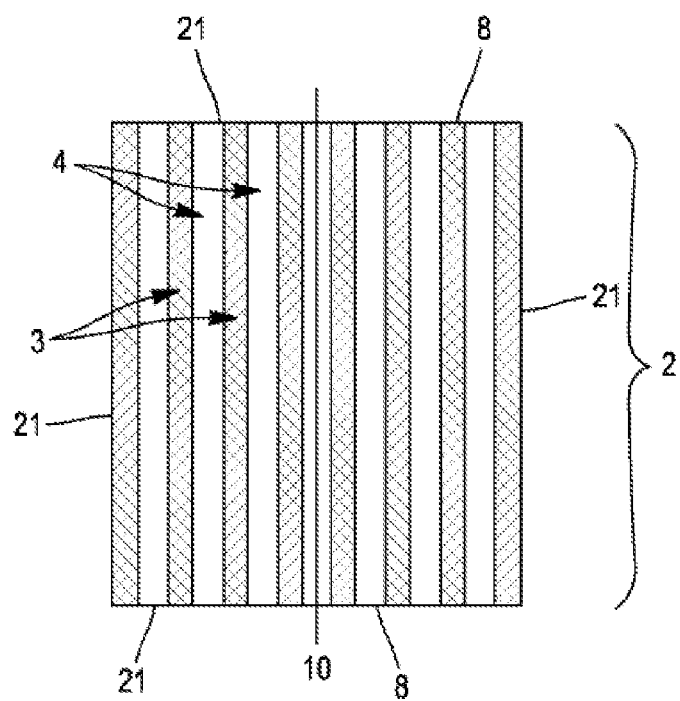
FIG. 2 is a diagrammatic representation of a top view of the array of leaves and slits of the multileaf collimator in FIG. 1, illustrating the entrance face of the array of leaves and slits.

FIG. 2 is a diagrammatic representation of a top view of the array 2 of leaves 3 and slits 4 of the multileaf collimator 1 illustrating the entrance face of the array 2.

Figure 3:
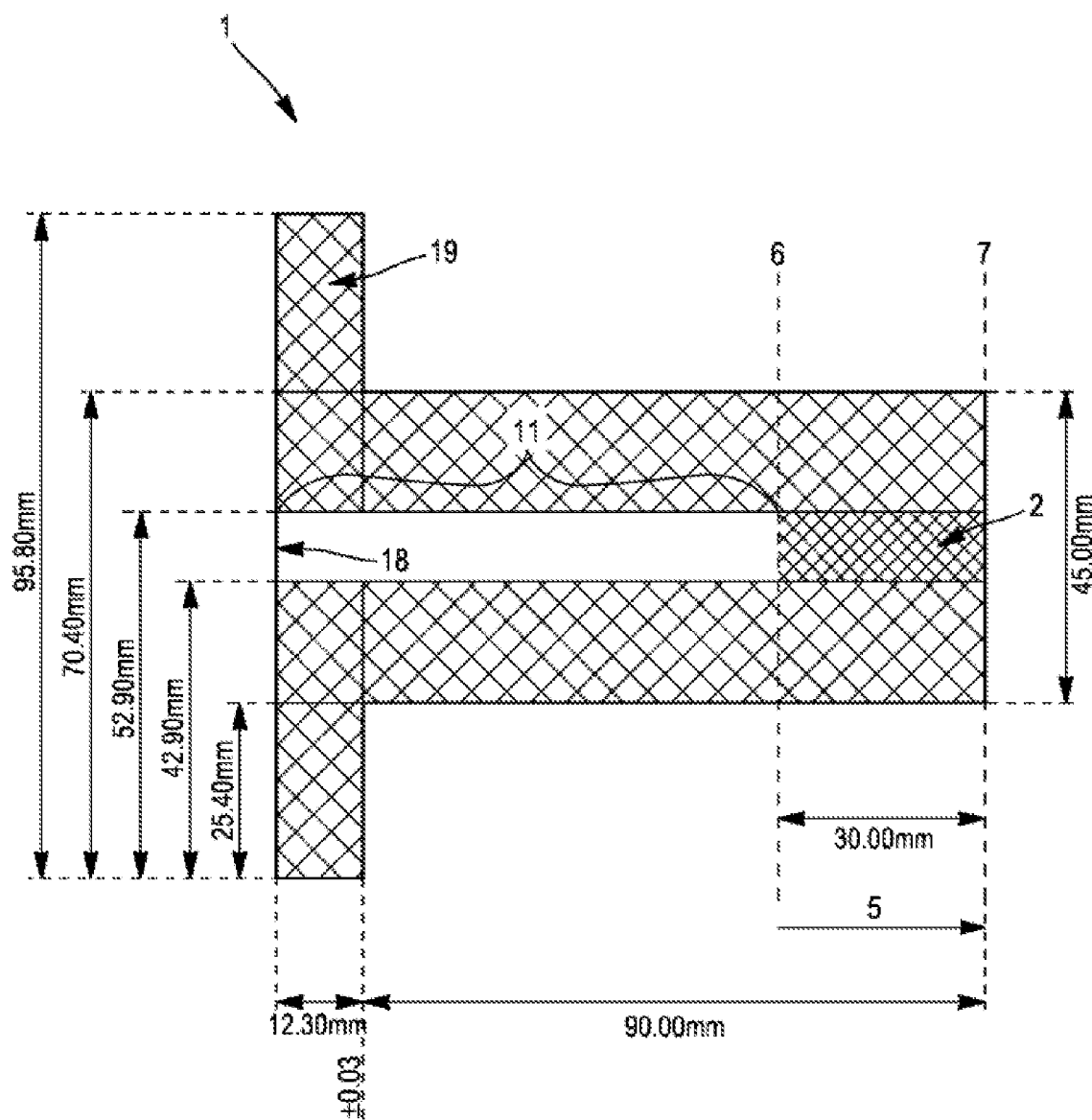
FIG. 3 is a diagrammatic representation of a sectional view of the multileaf collimator in FIG. 1.

FIG. 3 is a diagrammatic representation of a sectional profile view of the multileaf collimator 1.

As illustrated in FIG. 3, the multileaf collimator 1 further comprises a channel 11 extending in the longitudinal direction 5 and located upstream of the entrance plane 6 of the array 2 with respect to the longitudinal direction 5 (i.e. on the side opposite the array 2 with respect to plane 6).

The channel 11 is oriented in the longitudinal direction 5 and extends:
from an entrance 18 of the channel 11, located upstream of the entrance plane 6 of the array 2 with respect to the longitudinal direction 5,
to the entrance plane 6 of the array 2.

The channel 11 has an axis of symmetry that coincides with the centre of the entrance face of the array 2, said entrance face being defined by the perimeter 21 of the array 2 in the entrance plane 6 of the array 2.

The walls of the multileaf collimator 1 surrounding channel 11 have a thickness between 6 and 0.5 cm, preferably between 3 and 1 cm, said thickness being 1.75 cm in the embodiment illustrated in FIG. 3.

The length of the channel 11 is to be understood as the length between the entrance 18 of channel 11 and the entrance plane 6 of the array 2. The length of channel 11 is comprised between 1 and 10 cm, preferably between 3 and 8 cm, more preferably between 4 and 7 cm, and it is 6 cm in the embodiment illustrated in FIG. 3.

It should be noted that a portion forming a flange 19 extends on either side of the multileaf collimator 1 in a plane perpendicular to the longitudinal direction 5; said perpendicular plane being located at the level of the entrance 18 of the channel 11. This portion forming a flange 19 extends perpendicularly to the longitudinal direction 5 over a distance comprised between 10 and 1 cm, preferably between 5 and 2 cm, this distance being 2.54 cm in the embodiment presented.

In the embodiment as illustrated in FIG. 3, a distance, in the longitudinal direction 5, between the entrance plane 6 of the array 2 and the exit plane 7 of the array 2 is comprised between 1 and 6 cm, preferably between 2 and 4 cm, the distance being equal to 3 cm in the particular embodiment presented.

All the dimensions indicated in FIG. 3 are in millimetres.

Figure 4:
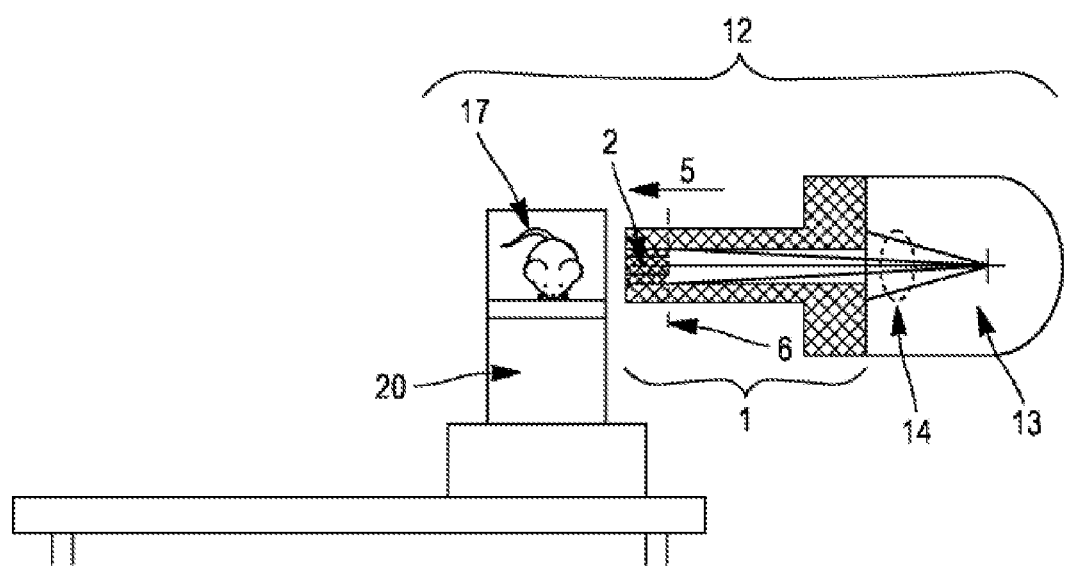
FIG. 4 is a diagrammatic representation in side view of a device according to the invention comprising the multileaf collimator in FIG. 1.

FIG. 4 is a diagrammatic profile representation of a device 12 according to a particular embodiment comprising the array 2 of leaves 3 and slits 4 according to the embodiment illustrated in FIGS. 1 and 2, and the multileaf collimator 1 according to the embodiment illustrated in FIG. 3.

The device 12 comprises a source 13 of emission of an incident electromagnetic beam 14 and/or a source 13 of emission of an incident beam 14 of subatomic particles, the source 13 being arranged for emitting said incident beam 14 in the direction of the entrance plane 6 of the array.

The multileaf collimator 1 is arranged to obtain, on the side of the exit plane 7, an arrangement of beams 22 starting from the incident beam 14 located on the side of the entrance plane 6.

The incident beam 14 is emitted in the direction of the entrance 18 of the channel 11 in a mean direction parallel to the longitudinal direction 5, in such a way that the axis of revolution of the incident beam 14 is parallel to the channel 11 of the multileaf collimator 1.

According to the embodiment illustrated, the source 13 emits a divergent incident beam 14. Advantageously, the divergence of the incident beam 14 is greater than 0.1 degrees, typically greater than 5 degrees, and/or preferably less than 45 degrees, the divergence being 20° in the embodiment presented in FIG. 4.

Each beam of the arrangement of beams 22 (leaving each of the slits 4) has a divergence less than that of the incident beam 14, preferably less than 10 degrees, preferably less than 5 degrees, preferably less than 0.1 degrees, and preferably zero.

The arrangement of beams 22, according to the embodiment illustrated, has, in the exit plane 6, a width greater than 1 mm, preferably comprised between 1 mm and 10 cm, preferably between 1 and 5 cm, this width being 1.2 cm with a square shape in the embodiment presented. The arrangement of beams 22 obtained is commonly denoted by a person skilled in the art by the term "array of minibeams".

In the embodiment illustrated in FIG. 4, the source 13 of electromagnetic radiation is an X-ray source. Advantageously, the X-ray source 13 is a cathode source SARRP of reference VARIAN NDI-225-22, composed of an X-ray tube with a maximum voltage of 220 kV and a current of 13 mA.

The incident beam 14 has an average energy of several tens of key, a dose rate at the centre of 0.82 Gy/min at a distance of 35 cm from the source and for a field size of 0.5 mm, a total field area of about 4×4 cm$^2$ and a divergence of 20°.

Figure 5:
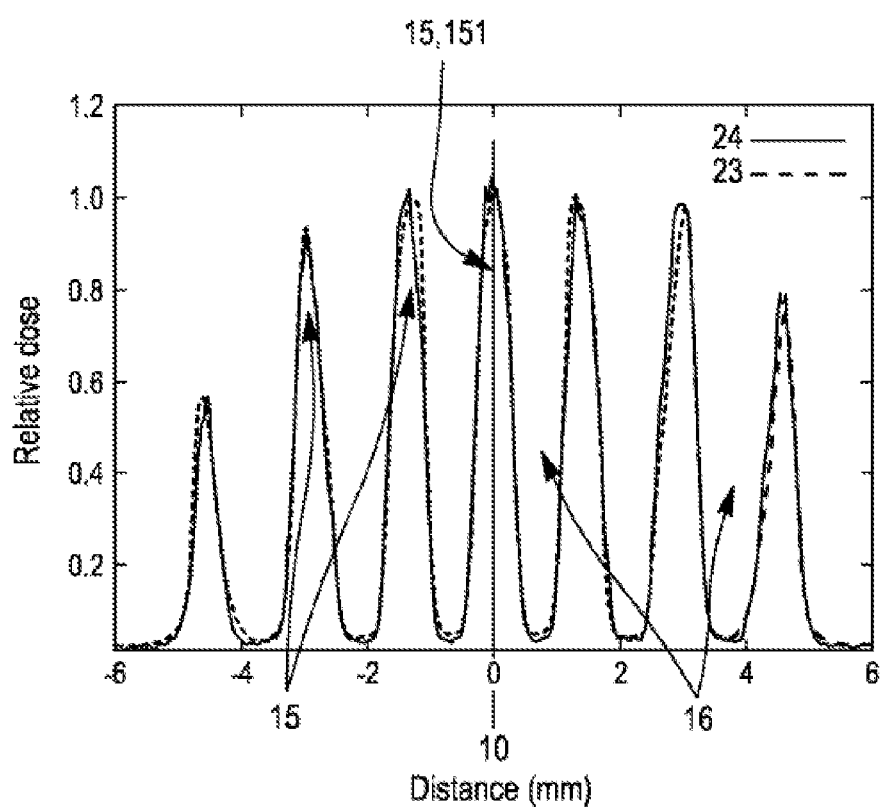
FIG. 5 is a graph representing a transverse dose profile of the arrangement of beams 22 in a plane:
  for a simulated matrix of minibeams obtained from data, relating to the arrangement of a device according to the invention, calculated from a Monte-Carlo algorithm;
  for a matrix of minibeams measured from a multileaf collimator according to the invention made on the basis of said calculated data.

FIG. 5 is a graph representing a transverse dose profile (in arbitrary units) of the arrangement of beams 22 in a plane located downstream of the exit plane 7 of the array 2 (i.e. on the side opposite the array 2 with respect to the plane 7) and at a depth of 1 cm in a water phantom:
for a simulated matrix of minibeams obtained from data relating to the arrangement of the device 12 calculated from a Monte-Carlo algorithm (curve 23), in a water phantom at 1 cm depth,
for a matrix of minibeams measured from a multileaf collimator 1 made on the basis of said calculated data (curve 24), in a water phantom at 1 cm depth.

According to the invention, the device 12 makes it possible to obtain the arrangement of beams 22 forming an alternation of high-energy lines and lower-energy lines 16 (this lower energy possibly being zero).

The arrangement of beams 22 is a one-dimensional matrix of beams, i.e. an alternation of beams (of high energy and of lower energy) in a spatial direction.

The quasi-superposition of the transverse dose profile of the simulated matrix of minibeams 23, shown with dotted lines, and the measured matrix of minibeams 24, shown with solid lines should be noted.

It should be noted that the transverse profile of energy or of dose of the low-energy lines 16 in matter, in particular in a water phantom at 1 cm depth in the case of the example illustrated in FIG. 5, is not zero, because particles derived from the high-energy lines 15 adjacent to the low-energy lines 16 are scattered in matter.

According to the embodiment illustrated, the maximum energy of the higher-energy line 15, 151 is at least ten times greater than the minimum energy of the lower-energy line 16 at 1 cm depth in a water phantom. Advantageously, the maximum energy of the higher-energy line 151 may be at least 20 times greater than the minimum energy of the lower-energy line 16.

The ratio of the maximum energy of a high-energy line 15 to the maximum energy of a low-energy line 16 is commonly denoted by a person skilled in the art as "peak to valley ratio"; the term valley referring to a low-energy line 16 and the term peak to a high-energy line 15.

According to the embodiment, the full width at half maximum of a peak 15 is close to 0.7 mm, at 1 cm depth in a water phantom, and the full width at half maximum of a valley 16 is close to 0.7 mm, at 1 cm depth in a water phantom.

Advantageously, at 1 cm depth in a water phantom, the full width at half maximum of an energy peak 15 is between 300 and 800 µm, preferably between 400 and 700 µm, more preferably between 400 and 600 µm; the full width at half maximum of an energy valley 16 is between 300 and 800 µm, preferably between 400 and 700 µm, more preferably between 400 and 600 µm.

Advantageously, the full width at half maximum of the valleys will be equal to the full width at half maximum of the peaks.

Advantageously, the device 12 comprises a support 20, on which the target 17 intended to be irradiated may be placed, said support 20 being movable in translation and/or in rotation with respect to the arrangement of beams 22. Advantageously, the support 20 makes it possible to approach the target 17 to a distance less than 20 cm from an exit of the multileaf collimator 1. This approaching has the effect of increasing the dose rate delivered to the target 17 by a minimum factor of 3. Said support 20 may also make it possible, by rotating it, to carry out interlaced irradiations of the target 17.

An embodiment will now be described of a method of making a multileaf collimator 1 according to the invention illustrated in FIGS. 1, 2 and 3, the multileaf collimator 1 being intended to be incorporated in the device 12 according to the invention illustrated in FIG. 4.

This method comprises:
acquisition, in technical calculation means, of parameters characterizing the source 13,
acquisition, in the technical calculation means, of parameters characterizing respectively:
  a desired arrangement of beams 22 leaving the multileaf collimator 1 and/or at the level of a target 17, or the multileaf collimator 1,
acquisition, in the technical calculation means, of parameters characterizing the target 17,
at least one step of calculation, by the technical calculation means, of characteristics respectively:
  of the multileaf collimator 1 as a function of acquired parameters in particular concerning the desired arrangement of beams 22, or
  of the desired arrangement of beams 22, by successive iterations of the step of acquisition of the parameters characterizing the multileaf collimator 1.

In the present description, by "technical calculation means" is meant any processing unit, or equivalent system, able to carry out one or more steps of calculation. The "calculation means" only comprise technical means, preferably electronic means (analogue and/or digital), a central processing unit of a computer, a microprocessor, and/or software means.

By acquired parameters characterizing the desired arrangement of beams 22, or calculated characteristics of the desired arrangement of beams 22, is meant in particular:
  a size of the arrangement of beams 22, and/or
  a full width at half maximum of a high-energy line 15, and/or
  a full width at half maximum of a low-energy line 16, and/or
  a ratio of the maximum energy of a high-energy line 15 to the maximum energy of a low-energy line 16.

By parameters characterizing the source 13 is meant in particular:
  a voltage of the source 13, and/or
  a current of the source 13, and/or
  a mean dose rate of the source 13, and/or
  a divergence of the source 13, and/or
  a field size of the source 13.

By parameters characterizing the target 17 is meant in particular:
  absorption coefficients of the materials of the target 17 with respect to the wavelengths of the incident beam 14 emitted by the source 13, and/or
  a distance traversed in the target 17 by the arrangement of beams 22.

By parameters characterizing the multileaf collimator 1, or calculated characteristics of the multileaf collimator 1, is meant in particular:
  a number of slits 4, and/or
  a number of leaves 3, and/or
  a length of the channel 11, in the longitudinal direction 5, between an entrance 18 of the channel 11 and the entrance plane 6 of the array 2, and/or
  a distance, in the longitudinal direction 5, between the entrance plane 6 of the array 2 and the exit plane 7 of the array 2, and/or
  a thickness of each leaf 3 as a function of a coordinate in the longitudinal direction 5, and/or
  a thickness of each slit 4 as a function of a coordinate in the longitudinal direction 5.

The acquired parameters or the calculated characteristics may also comprise, in addition:
  a full width at half maximum of the incident beam 14 emitted by the source 13 (parameter characterizing the source 13), and/or
  a divergence of the incident beam 14 emitted by the source 13 (parameter characterizing the source 13), and/or
  a profile of the energy spectrum of the incident beam 14 emitted by the source 13 (parameter characterizing the source 13), and/or
  a distance between the source 13 and the entrance plane 6 of the multileaf collimator 1 (parameter characterizing the device 12), and/or
  a distance between the multileaf collimator 1 and the target 17 (parameter characterizing the device 12),
  a distance between the source 13 and the inlet of the channel 11 (parameter characterizing the device 12),
  a distance between the source 13 and the target 17 (parameter characterizing the device 12).

The at least one calculation step may further comprise calculation of the relative positions of the source 13, of the multileaf collimator 1 and/or of the target 17.

The at least one calculation step is carried out on the basis of a Monte-Carlo algorithm.

The arrangement and the distances of the array 2 as presented in FIG. 1 are obtained by carrying out the method according to the invention using a Monte-Carlo algorithm, with Geant4 code version 9.1, so as to obtain a full width at half maximum of the high-energy lines 15 equal to 700 µm at 1 cm depth in a water phantom and a full width at half maximum of a low-energy line 16 equal to 700 µm at 1 cm depth in a water phantom, by successive iterations of the step of acquisition of the parameters characterizing the multileaf collimator 1, which are the thickness of each leaf 3 as a function of a coordinate in the longitudinal direction 5 and the thickness of each slit 4 as a function of a coordinate in the longitudinal direction 5, and starting from the following acquired parameters:

a field size of the source 13 of 2.3 mm,
  a divergence of the source 13 of 20°,
  a distance of 174.75 mm between the source 13 and the exit plane 7 of the multileaf collimator 1,
  a distance of 30 mm between the exit plane 7 of the multileaf collimator 1 and the target 17,
  a length of channel 11 of 72.3 mm,
  a number of slits 4 equal to 7,
  a number of leaves 3 equal to 6,
  an energy spectrum of the source calculated from the SpekCal software.

The Monte-Carlo algorithm is programmed so as to:
  optimize the ratio of the maximum energy of a high-energy line 15 to the maximum energy of a low-energy line 16,
  homogenize the maximum energies of the high-energy lines 15,
  reduce the lateral penumbra effects at the interfaces between the high-energy lines 15 and the low-energy lines 16.

Of course, the invention is not limited to the examples which have just been described and numerous adjustments can be made to these examples without exceeding the scope of the invention.

Thus, in variants of the embodiments described above that may be combined together:
  the entrance plane 6 and exit plane 7 of the array 2 as illustrated in FIG. 1 may not be parallel, and/or
  the opposite internal walls 8 between which the leaves extend as illustrated in FIG. 2 may not be parallel, and/or
  the multileaf collimator 1 as shown in FIG. 3 may be made of any of the materials known to a person skilled in the art, for example such as any metal, such as tungsten, metal alloys, for example brass or Wood's metal, also called Lipowitz alloy, and/or
  the multileaf collimator 1 as shown in FIG. 3 may be made by any technique known to a person skilled in the art such as, in addition, spark erosion machining and/or piercing and/or assembly of leaves, and/or
  the array 2 of leaves 3 and slits 4 of the multileaf collimator 1 as shown in FIGS. 1 and 2 may generally comprise at least three slits 4 and/or at least two leaves 3, and/or
  a thickness of at least one slit 4 (preferably of several slits 4, at least those nearest to plane 10) of the array 2 may vary in the longitudinal direction 5, and/or
  at least one slit 4 (preferably several slits 4, at least those nearest to plane 10) of the array 2 may have a thickness in the entrance plane 6 of the array 2 different from a thickness in the exit plane 7 of the array 2, and/or
  the array 2 may not be symmetrical with respect to the central plane 10 of the array 2, and/or
  the multileaf collimator 1 may further comprise a stopper designed to be arranged, preferably detachably, on the multileaf collimator 1 downstream of the exit plane 7 of the array 2, said stopper being arranged to delimit the size and/or shape of a beam leaving the multileaf collimator 1. The stopper is preferably made of the same material of which the multileaf collimator 1 is made, and/or
  the source 13 as illustrated in FIG. 4 may be:
    a source of electromagnetic radiation such as an X-ray or gamma ray source, or
    a source of emission of an incident beam 14 of subatomic particles such as, among others, a source of electrons or a source of protons, and/or
  the multileaf collimator 1 may be designed to be arranged, preferably detachably, in the vicinity of an exit of the incident beam 14 emitted by the source 13, and/or
  any analytical algorithm or numerical simulation or probabilistic algorithm, such as, in addition, the Monte Carlo, Las Vegas or Atlantic City algorithm, may be used for carrying out the at least one calculation step, and/or
  the target 17 may be located inside an object; the absorption coefficient of the object, if it is different from that of the target, may constitute a parameter to be acquired. In this case, the distance that the beam will have to travel in the object, before being propagated to the target, may be a parameter to be acquired, and/or
  the size of the target may also constitute a parameter to be acquired.

Moreover, the various characteristics, forms, variants and embodiments of the invention may be combined together in various combinations provided they are not incompatible or mutually exclusive.

The invention claimed is:

1. A device comprising:
  a multileaf collimator, said multileaf collimator comprising an array of leaves and slits, said array comprising an alternation of leaves and slits and extending in a longitudinal direction, said longitudinal direction being defined as a direction extending from an entrance plane of the array to an exit plane of the array, each leaf being located between two slits;
  at least one leaf or at least one slit of the array has a thickness different from a thickness respectively of at least one other leaf or at least one other slit of the array in the entrance plane or exit plane of the array; and
  a thickness of at least one leaf or a thickness of at least one slit of the array varies in the longitudinal direction;
  said device having a source of emission of an incident electromagnetic beam or a source of emission of an incident beam of subatomic particles, said source being arranged for emitting the beam in the direction of the entrance plane of the array, said multileaf collimator being arranged for obtaining, from the incident beam, a desired arrangement of beams at a target; and
  the arrangement of beams constitutes an array of minibeams for radiotherapy treatment and forms an alternation of high-energy lines and lower-energy lines;
  and at least one slit/leaf interface of the array is parallel to at least another slit/leaf interface of the array, said at least one slit/leaf interface and said at least another slit/leaf interface are formed at a non-zero angle relative to a central plane of the array, the central plane of the array being parallel to the longitudinal direction and linking two opposite internal walls of the multileaf collimator between which the leaves extend.

2. The device according to claim 1, wherein the source emits a divergent incident beam.

3. The device according to claim 1, wherein the arrangement of beams has a width greater than 1 mm or less than 10 cm.

4. The device according to claim 1, wherein the source of electromagnetic radiation is an X-ray source.

5. The device according to claim 4, wherein the X-ray source is a cathode source.

6. The device according to claim 1, wherein the multileaf collimator has a channel extending in the longitudinal direction and located upstream of the entrance plane of the array.

7. The device according to claim 1, wherein the thickness of each of the leaves of the array in any one of the planes perpendicular to the longitudinal direction is greater than 300 μm or less than 2 mm.

8. The device according to claim 1, wherein a distance, in the longitudinal direction, between the entrance plane of the array and the exit plane of the array is greater than 1 cm or less than 6 cm.

9. The device according to claim 1, wherein at least one leaf of the array has a thickness that is different from a thickness of at least one other leaf of the array in the entrance plane of the array.

10. The device according to claim 1, wherein at least one leaf of the array has a thickness that is different from a thickness of at least one other leaf of the array in the exit plane of the array.

11. The device according to claim 1, wherein at least one leaf of the array has a thickness in the entrance plane of the array different from a thickness in the exit plane of the array.

12. The device according to claim 1, wherein the thickness of each of the slits of the array in any one of the planes perpendicular to the longitudinal direction is greater than 300 μm or less than 1 mm.

13. The device according to claim 1, wherein at least one slit of the array has a thickness in the entrance plane of the array different from a thickness of at least one other slit of the array in the entrance plane of the array.

14. The device according to claim 1, wherein:
at least one slit of the array has a thickness in the exit plane of the array different from a thickness of at least one other slit of the array in the exit plane of the array, or
at least one slit of the array has a thickness in the exit plane of the array different from a thickness of at least one other slit of the array in the exit plane of the array and at least one slit of the array has a thickness in the entrance plane of the array different from a thickness in the exit plane of the array.

15. The device according to claim 1, wherein at least one slit of the array has a thickness in the entrance plane of the array different from a thickness in the exit plane of the array.

16. The device according to claim 1, wherein the successive leaves of the array have respective thicknesses in any one of the planes perpendicular to the longitudinal direction that vary in an increasing manner or that remain constant with increasing distance from the central plane of the array in two opposite directions perpendicular to the central plane of the array, the central plane of the array being parallel to the longitudinal direction and linking two opposite internal walls of the multileaf collimator between which the leaves extend.

17. The device according to claim 16, wherein the lower energy lines have an energy equal to zero or close to zero.

18. The device according to claim 1, wherein the successive slits of the array have respective thicknesses in any one of the planes perpendicular to the longitudinal direction that vary in an increasing manner or that remain constant with increasing distance from the central plane of the array in two opposite directions perpendicular to the central plane of the array, the central plane of the array being parallel to the longitudinal direction and linking two opposite internal walls of the multileaf collimator between which the leaves extend.

19. The device according to claim 1, wherein the successive slit and leaf interfaces form respective angles with respect to the central plane of the array that vary in an increasing manner or that remain constant with increasing distance from the central plane of the array in two opposite directions perpendicular to the central plane of the array, each of these angles having its vertex upstream of the entrance plane of the array with respect to the longitudinal direction, the central plane of the array being parallel to the longitudinal direction and linking two opposite internal walls of the multileaf collimator between which the leaves extend.

20. The device according to claim 1, further comprising a stopper arranged to be fitted detachably on the collimator downstream of the exit plane of the array with respect to the longitudinal direction, said stopper being arranged for delimiting a size or shape of an arrangement of beams leaving the multileaf collimator.

21. A method of making a multileaf collimator comprising an array of leaves and slits, said array comprising an alternation of leaves and slits and extending in a longitudinal direction, said longitudinal direction being defined as a direction extending from an entrance plane of the array to an exit plane of the array, each leaf being located between two slits; the multileaf collimator including:
at least one leaf or at least one slit of the array has a thickness different from a thickness respectively of at least one other leaf or at least one other slit of the array in the entrance plane or exit plane of the array;
a thickness of at least one leaf and/or a thickness of at least one slit of the array varies in the longitudinal direction; and
and at least one slit/leaf interface of the array is parallel to at least another slit/leaf interface of the array, said at least one slit/leaf interface and said at least another slit/leaf interface are formed at a non-zero angle relative to a central plane of the array, the central plane of the array being parallel to the longitudinal direction and linking two opposite internal walls of the multileaf collimator between which the leaves extend, the multileaf collimator being intended to be the collimator of a device according to claim 1, said method comprising:
acquisition, in technical calculation means, of parameters characterizing the source;
acquisition, in the technical calculation means, of parameters characterizing the multileaf collimator;
acquisition, in the technical calculation means, of parameters characterizing a target;
at least one step of calculation, by the technical calculation means, of characteristics of the desired arrangement of beams, at the target, that constitutes an array of minibeams for radiotherapy treatment and forms an alternation of high-energy lines and lower-energy lines, by successive iterations of the step of acquisition of the parameters characterizing the multileaf collimator; and
manufacture of said multileaf collimator.

22. The method according to claim 21, wherein the acquired parameters characterizing the desired arrangement of beams or the calculated characteristics of the desired arrangement of beams, further comprise:
- a size of the arrangement of beams, and/or
- a full width at half maximum of a high-energy line, and/or
- a full width at half maximum of a low-energy line, and/or
- a ratio of a maximum energy of a high-energy line to a maximum energy of a low-energy line.

23. The method according to claim 21, wherein the parameters characterizing the source further comprise:
- a voltage of the source, and/or
- a current of the source, and/or
- a mean dose rate of the source, and/or
- a divergence of the source, and/or
- a field size of the source.

24. The method according to claim 21, wherein the acquired parameters characterizing the multileaf collimator or the calculated characteristics of the multileaf collimator, further comprise:
- a number of slits, and/or
- a number of leaves, and/or
- a length of a channel, in the longitudinal direction, between an entrance of the channel and the entrance plane of the array, and/or
- a distance, in the longitudinal direction, between the entrance plane of the array and the exit plane of the array, and/or
- a thickness of each leaf as a function of a coordinate in the longitudinal direction, and/or
- a thickness of each slit as a function of a coordinate in the longitudinal direction.

25. The method according to claim 21, wherein the multileaf collimator is manufactured by spark erosion machining, piercing or assembly of leaves.

26. The method according to claim 21, wherein the at least one calculation step is carried out on the basis of a Monte-Carlo algorithm.

27. A method of making a multileaf collimator comprising an array of leaves and slits, said array comprising an alternation of leaves and slits and extending in a longitudinal direction, said longitudinal direction being defined as a direction extending from an entrance plane of the array to an exit plane of the array, each leaf being located between two slits; the multileaf collimator including:
- at least one leaf or at least one slit of the array has a thickness different from a thickness respectively of at least one other leaf or at least one other slit of the array in the entrance plane or exit plane of the array, and
- a thickness of at least one leaf and/or a thickness of at least one slit of the array varies in the longitudinal direction, the multileaf collimator being intended to be the collimator of a device according to claim 1, said method comprising:

acquisition, in technical calculation means, of parameters characterizing the source;

acquisition, in the technical calculation means, of parameters characterizing a desired arrangement of beams leaving the multileaf collimator and/or at the level of a target, said arrangement of beams constitutes an array of minibeams for radiotherapy treatment and forms an alternation of high-energy lines and lower-energy lines;

acquisition, in the technical calculation means, of parameters characterizing the target;

at least one step of calculation, by the technical calculation means, of characteristics of the multileaf collimator as a function of acquired parameters in particular concerning the desired arrangement of beams; and manufacture of said multileaf collimator.

28. The device according to claim 1, wherein at least one of a full width at half maximum of a high-energy line and a full width at half maximum of a low-energy line, is between 300 to 800 μm.

29. The device according to claim 1, wherein a maximum energy of at least one of the higher-energy lines is at least ten times greater than the minimum of the lower-energy lines.

* * * * *